(12) United States Patent
La Rosa et al.

(10) Patent No.: US 12,285,534 B2
(45) Date of Patent: Apr. 29, 2025

(54) METHODS AND DEVICES FOR SANITIZATION

(71) Applicants: STMicroelectronics (Grenoble 2) SAS, Grenoble (FR); STMicroelectronics S.r.l., Agrate Brianza (IT)

(72) Inventors: Roberto La Rosa, Viagrande (IT); Jean Camiolo, St. Egreve (FR); Laurent Yvan Louis Jamet, Saint Martin d Heres (FR)

(73) Assignees: STMicroelectronics S.r.l., Agrate Brianza (IT); STMicroelectronics (Grenoble 2) SAS, Grenoble (FR)

( * ) Notice: Subject to any disclaimer, the term of this patent is extended or adjusted under 35 U.S.C. 154(b) by 840 days.

(21) Appl. No.: 17/328,435

(22) Filed: May 24, 2021

(65) Prior Publication Data
US 2022/0370669 A1    Nov. 24, 2022

(51) Int. Cl.
- *A61L 2/24* (2006.01)
- *A61L 2/10* (2006.01)
- *G08C 17/02* (2006.01)
- *G08B 7/06* (2006.01)

(52) U.S. Cl.
CPC .................. *A61L 2/24* (2013.01); *A61L 2/10* (2013.01); *G08C 17/02* (2013.01); *A61L 2202/11* (2013.01); *A61L 2202/14* (2013.01); *G08B 7/06* (2013.01)

(58) Field of Classification Search
CPC ..... A61L 2/10; A61L 2/24; A61L 2/26; A61L 2/28; A61L 2202/11; A61L 2202/14; G08C 17/00; G08C 17/02
See application file for complete search history.

(56) References Cited

U.S. PATENT DOCUMENTS

| | | |
|---|---|---|
| 6,592,816 B1 | 7/2003 | Ebel |
| 8,067,750 B2 | 11/2011 | Deal |
| 10,228,622 B2 | 3/2019 | Kimsey-Lin |
| 2004/0227057 A1 | 11/2004 | Tuominen |

(Continued)

FOREIGN PATENT DOCUMENTS

| | | |
|---|---|---|
| AU | 2017100912 A4 | 8/2017 |
| CA | 2399851 C | 4/2003 |

(Continued)

*Primary Examiner* — Timothy C Cleveland
(74) *Attorney, Agent, or Firm* — Slater Matsil, LLP (57) ABSTRACT

A system to sanitize a surface includes an emitter. The emitter of the system to sanitize the surface includes: a light source configured to generate light at a sanitizing wavelength; a receiver configured to receive a wireless signal; and a processing circuit for the emitter configured to turn the light source on, turn the light source off, and adjust an intensity of light generated by the light source depending on the wireless signal. The system to sanitize the surface further includes a sensor. The sensor of the system to sanitize the surface includes: a photoelectric transducer configured to convert light at the sanitizing wavelength to a current; and a processing circuit for the sensor powered by the current and in communication with a transmitter to transmit the wireless signal, the processing circuit for the sensor being configured to control emission of the wireless signal depending on a power level supplied by the current.

20 Claims, 7 Drawing Sheets

(56) References Cited

U.S. PATENT DOCUMENTS

| | | |
|---|---|---|
| 2006/0037380 A1 | 2/2006 | Bulst et al. |
| 2011/0168898 A1* | 7/2011 | Statham .................... A61L 2/24 |
| | | 250/354.1 |
| 2016/0183351 A1 | 6/2016 | Snyder et al. |
| 2019/0091738 A1 | 3/2019 | Chen |
| 2020/0367334 A1* | 11/2020 | Glowczwski .......... H05B 45/12 |
| 2023/0277702 A1* | 9/2023 | Wendt ...................... A61L 2/28 |
| | | 422/24 |

FOREIGN PATENT DOCUMENTS

| | | |
|---|---|---|
| CN | 1269246 A | 10/2000 |
| CN | 109121273 A | 1/2019 |
| CN | 109532415 A | 3/2019 |
| WO | 2019079065 A1 | 4/2019 |
| WO | 2019178639 A1 | 9/2019 |

\* cited by examiner

METHODS AND DEVICES FOR SANITIZATION

TECHNICAL FIELD

The present invention relates generally to a systems and method for sanitizing a surface. In particular, this invention relates to systems and methods for using light emissions at a sanitizing wavelength to sanitize a surface.

BACKGROUND

Generally, a light may be used to sanitize a surface. This may provide a quick solution for sanitizing or disinfecting spaces. However, disinfecting and sanitization benefits may depend on the length of exposure of a surface to a sanitizing wavelength and the intensity of the light exposure. It is, thus, advantageous to know the intensity and length of time a surface receives light at a sanitizing wavelength.

SUMMARY

In accordance with an embodiment of the present invention, a method for sanitizing a surface includes: directing a light towards the surface; using the light to power a sensor located on the surface; generating, by the sensor, a wireless signal that depends on an intensity of the light received by the sensor; and adjusting the light depending on the wireless signal.

In accordance with an embodiment of the present invention, a system to sanitize a surface includes an emitter including: a light source configured to generate light at a sanitizing wavelength; a receiver configured to receive a wireless signal; and a processing circuit for the emitter configured to turn the light source on, turn the light source off, and adjust an intensity of light generated by the light source depending on the wireless signal. The system to sanitize the surface further includes a sensor including: a photoelectric transducer configured to convert light at the sanitizing wavelength to a current; and a processing circuit for the sensor powered by the current and in communication with a transmitter to transmit the wireless signal, the processing circuit for the sensor being configured to control emission of the wireless signal depending on a power level supplied by the current.

In accordance with an embodiment of the present invention an energy-autonomous sensor for a closed-loop sanitization operation includes: a photoelectric transducer configured to convert light at a sanitizing wavelength into a current; a transmitter to emit a wireless signal; and a processing circuit powered by the current and in communication with the transmitter, the processing circuit being configured to control emission of the wireless signal depending on a power level supplied by the current.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The importance of working, living, and functioning in sanitary environments has never been greater. Obviously, in the medical field, proper sanitization can reduce the risk of infection and greatly improve health outcomes. Routine sanitization is also critical for food preparation, childcare, elder care, and many other endeavors. In recent times, offices, schools, residences, event venues, and practically every forum for in-person human engagement have been faced with new needs to perform sanitization operations in new areas.

Many traditional sanitization methods involve the use of harsh chemicals. Chemicals are hard to use, may require storing potentially hazardous chemicals, and can become scarce when need drives demand high.

Light provides an alternative to traditional sanitization techniques. Applying an appropriate dosage of light at an appropriate wavelength can effectively sanitize an exposed area without some of the drawbacks of harsh chemicals. For example, UV light may be used to kill to viral and bacterial pathogens. Using light at a sanitizing wavelength does not require using or storing harsh chemicals. And, using light emissions for sanitization may does not pose the same scarcity risks present for chemical sanitization. Further, with the appropriate dosage and intensity, light can provide more effective sanitization than other methods.

Figure 1:
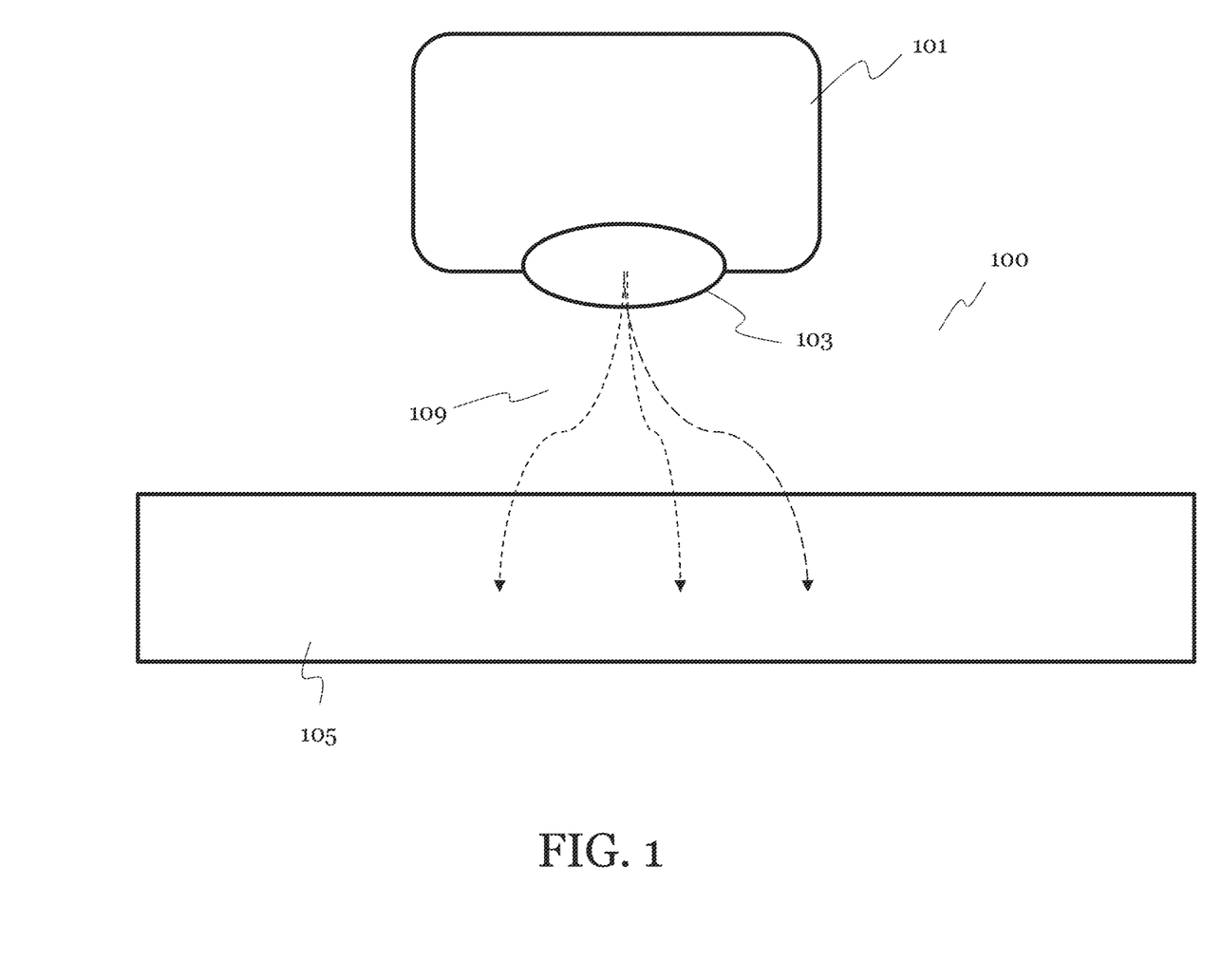
FIG. 1 shows an example of an open-loop system to sanitize a surface using a light source FIG. 2. depicts a closed-loop system for sanitizing a surface using a light source of an embodiment of the present invention.

FIG. 1 shows an example of an open-loop system to sanitize a surface using a light source.

As shown in FIG. 1, an open-loop system 100 includes an emitter 101. The emitter can include a light source 103 to generate light with a sanitizing wavelength. When the light source 103 is activated, or turned on, light at a sanitizing wavelength may be directed to a surface 105 to sanitize the surface. For proper sanitization light at a sanitizing wavelength needs to be applied for an appropriate time and at an appropriate intensity.

The system depicted in FIG. 1, however, is an open-loop system. No feedback from the surface 105 is provided to the emitter 101. Consequently, it is unknown how long the surface 105 receives light with the appropriate intensity for sanitization. This may cause the surface to be under sanitized, or over sanitized. Under sanitization can pose health risks. And over sanitizing a surface may waste energy. However, a closed loop-system may allow feedback regarding the intensity and duration of an exposure, which may improve the efficiency and effectiveness of sanitization systems and methods.

Figure 2:
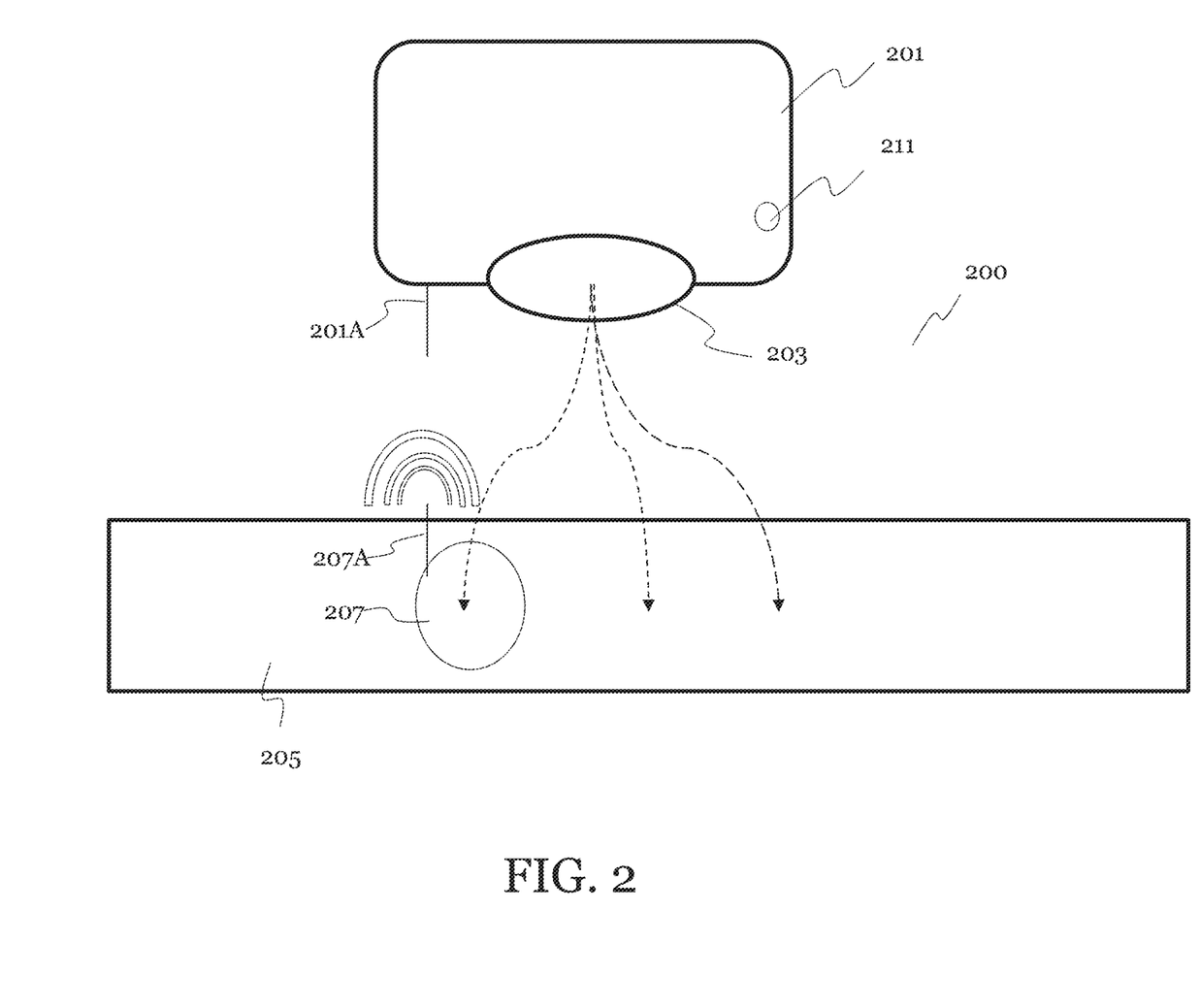

FIG. 2. depicts a closed-loop system for sanitizing a surface using a light source of an embodiment of the present invention.

The closed-loop system 200 may include an emitter 201. The emitter 201 may comprise a light source 203. When activated, or turned on, the light source 203 may generate light at a sanitizing wavelength that is directed to surface 205. The spectrum of wavelengths that have sanitizing properties is known to a person of ordinary skill in the art. For example, UV light may be used as a sanitizing wavelength. However, it should be appreciated that a desired wavelength for a sanitization operation may vary from application to application. The wavelength of the sanitizing light produced by the emitter 201 may vary in various embodiments. And, in various embodiments, the emitter may be configured to produce more than one range of wavelengths of light, each range for a different type of sanitization operation.

The closed-loop system 200 may further include a sensor 207. The sensor 207 may be positioned on the surface 205 to detect the intensity of the light at the sanitizing wavelength that arrives at the surface 205. The sensor 207 may include a transmitter 207A that broadcasts a wireless signal to the emitter 201. In various embodiments, the transmitter 207A may comprise a Bluetooth Low Energy transmitter. The emitter 201 may comprise a receiver 201A to pick up the wireless signal broadcast by the sensor 207. In various embodiments, the receiver 201A may comprise a Bluetooth Low Energy receiver.

The sensor 207, thus, may provide feedback to the emitter 201 to close the system loop. The emitter 201 may then adjust the intensity of light generated by the light source 203 depending on the wireless signal received from the sensor 207. For example, if the light intensity at the surface 205 falls below a desired range, the emitter 201 may increase the intensity of light generated by the emitter 201. If the light intensity received at the surface 205 is higher than a desired range, the emitter 201 may reduce the intensity of the light generated by the light source 203.

This allows the closed-loop system 200 to adjust depending on the real-time conditions at the sanitization target (the surface 205). The closed-loop system 200 may be used advantageously to improve the effectiveness of a sanitization by ensuring that the surface 205 receives the light at the sanitizing wavelength at an intensity sufficient to perform a sanitization operation and for a duration sufficient to perform the sanitization operation. The closed-loop system 200 also can improve the efficiency of a sanitization operation by reducing an intensity of the sanitizing light when it is unnecessarily high and stopping exposures when the desired duration has been reached. And, efficiency may be further improved by shutting off the light source 203 as soon as a surface has been exposed for an appropriate duration.

As will be appreciated by one of ordinary skill in the art, in various embodiments the desired intensity of light for the surface 205 may vary. Some applications may require more light intensity or less light intensity, shorter exposure duration or long exposure durations. The propensity of light to inactivate pathogens at different wavelengths and intensities is well documented. The desired intensity of light may depend on the type of sanitization operation. The desired intensity of light may comprise the intensity of light needed to accomplish the type of sanitization being performed. Similarly, a desired duration of light may comprise a duration needed to accomplish the type of sanitization being performed in conjunction with desired intensity of light. It should be appreciated that both the intensity and duration of the light may differ in various embodiments.

In various embodiments, the emitter 201 may trigger an alert if a sanitization process is unable to be performed. For example, if the light intensity of the light source has been increased to a maximum level allowed by the light source, and the light intensity reported by the sensor 207 falls below the desired sanitizing intensity, an alert may be triggered that the sanitization process is unable to be performed. In such cases, a user may move the emitter 201 closer to the surface or take other corrective action to attempt the sanitization process again.

In another example, the emitter 201 may produce an alert when a sanitization operation has been timed out. When a sanitization operation may not be performed within a desired time, an alert may be generated.

In various embodiments, the emitter may comprise a light emitting diode, LED 211. The LED may be turned on to indicate when a sanitizing operation cannot be completed. In other embodiments, the emitter 201 may comprise a user interface to alert a user that a sanitization operation may be performed. The emitter 201 may also emit an audible alert to indicate that a sanitization operation may not be completed.

The light source 203 used to generate the sanitizing wavelength may vary in different embodiments. For example, in various embodiments, the light source 203 may comprise an LED or arrangement of LEDs.

Figure 3:
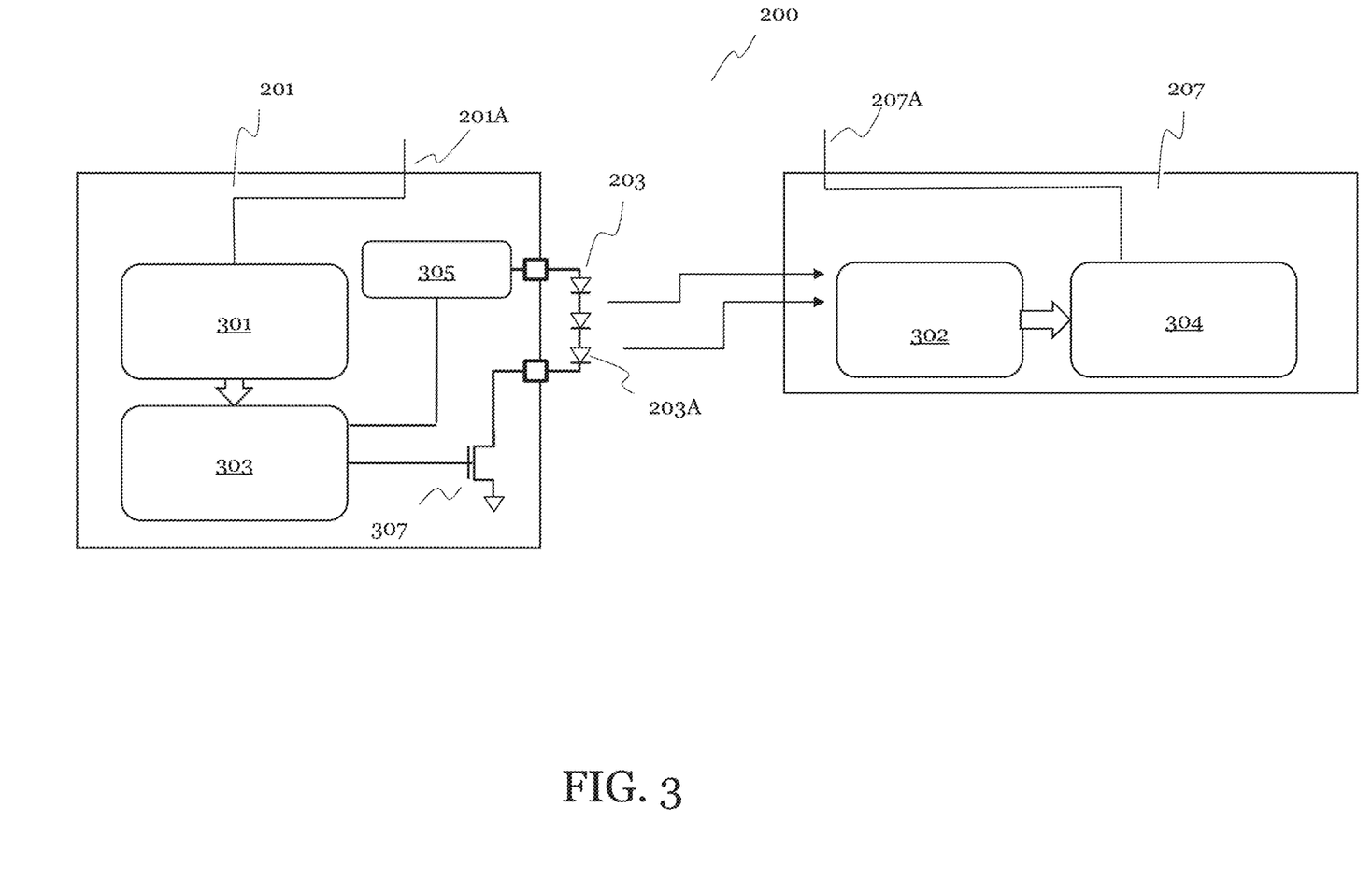
FIG. 3 depicts an embodiment of a closed-loop system in accordance with an embodiment of the present invention.

FIG. 3 depicts an embodiment of a closed-loop system 200 in accordance with an embodiment of the present invention.

In various embodiments, the emitter 201 may comprise a processing circuit 301. In various embodiments, the processing circuit may comprise a microcontroller, SoC, FPGA, DSP, or ASIC. In various embodiments, the processing circuit 301 may include the receiver 201A for wireless communication with the sensor 207.

The processing circuit 301 may be in communication with receiver 201A. The receiver 201A may detect a wireless signal emitted by sensor 207. The processing circuit 301 may also be in communication with the light source 203. Depending on the wireless signal generated by sensor 207, the processing circuit may to turn the light source 203 on, turn the light source off 203, and adjust an intensity of light generated by the light source 203 depending on the wireless signal received from the sensor 207.

To operate the light source 203, the processing circuit 301 may produce a pulse width modulation (PWM) signal. The processing circuit 301 may be in communication with a PWM controller 303. The processing circuit 301 may provide a PWM signal to the PWM controller 303. In turn, the PWM controller 303 may generate PWM pulses that are supplied to the light source 203. The duty cycle of the PWM pulses produced by the PWM controller 303 may be determined by the PWM signal produced by the processing circuit 301.

In this way, in various embodiments, the processing circuit 301 may control the intensity of light generated by the light source 203. When an increase in light intensity is desired, the duty cycle of the PWM pulses may be increased. Likewise, when a decrease in light intensity is desired, the duty cycle of the PWM pulses may be decreased.

The emitter 201 may have an internal power source. In various embodiments, the emitter 201 may comprise a battery. In various embodiments, the emitter 201 may also be coupled to a plug-in power source.

In various embodiments, the light source 203 may comprise an LED or arrangement of LEDs, like mentioned previously. The light source 203 may comprise a first LED 203A. Additional LEDs may also be included in the light source 203. The LEDs emit light having a wavelength that is determined by a wavelength range of the LED.

As will be appreciated, the wavelength of light emitted by an LED may depend on the materials and composition of the LED. LEDs may be utilized in the light source 203 to configure the light source to produce light at a desired wavelength for sanitization of the surface 205. The LEDs of a light source 203 may have a spectral range that corresponds to a sanitizing wavelength of light so that the LEDs produce light at a sanitizing wavelength. The intensity of light emitted by a light source 203 utilizing LEDs may depend on the duty cycle of the pulses activating the LEDs.

In various embodiments, the emitter 201 may also comprise an AC/DC power converter 305. The AC/DC power converter 305 may receiver AC pulses from the PWM controller 303 and convert them to DC power for the LEDs.

The emitter 201 may also comprise a transistor 307. The transistor may be controlled by the PWM controller 303 to facilitate operation of the light source 203. For example, the transistor 307 may comprise an NMOS transistor with a source coupled to a ground and a drain coupled to the light source 203. A gate of the NMOS transistor may be controlled by the PWM controller 303 to open and close a current path from the light source 203 to the ground thereby turning the light source 203 on and off. In various embodiments, the signal provided to the gate of the transistor 307 may be coordinated with the signal provided to the light source 203.

In various embodiments, it may be advantageous for the sensor 207 to be energy autonomous. An energy-autonomous sensor may operate without a battery or plug in energy source. This may be beneficial to reduce the need to replace batteries in a sensor. This may also reduce the cost and size of a sensor 207, which may allow them to be disposed in convenient locations. Also, it may allow a sensor 207 to be placed without regards to an outlet. And, energy independence for the sensor 207 may also be beneficial to reduce the cost of the sensor and make them easy to remove and replace. An energy autonomous sensor may also improve energy efficiency. In various embodiments, the sensor 207 may comprise an adhesive that allows it to be affixed to a target surface.

In various embodiments, the sensor 207 may comprise a photoelectric transducer 302. The photoelectric transducer 302 may allow the sensor 207 to be energy autonomous. The photoelectric transducer 302 converts light into a current that can be used to power the sensor 207 so no other power source may be needed.

In various embodiments the photoelectric transducer 302 may power a processing circuit 304 for the sensor 207. The processing circuit 304 may be in communication with the transmitter 207A. And, the processing circuit 304 may control emission of the wireless signal. Control of wireless emissions may depend on the intensity of light received by the sensor 207. In various embodiments, the processing circuit 304 may comprise a microcontroller, SoC, FPGA, DSP, or ASIC. The processing circuit 304 may include the transmitter 207A.

In various embodiments, the wireless signal broadcast by the sensor 207 may comprise a Bluetooth Low Energy Signal. In various embodiments the sensor 207 may comprise a Bluetooth Low Energy sensor. In various embodiments, the emitter 201 may comprise a Bluetooth Low Energy receiver. However, it will be appreciated that the embodiments of this disclosure are not limited to Bluetooth Low Energy devices. In various embodiments other types of sensors and emitters may be used.

In various embodiments, the power generated by the photoelectric transducer 302 may be a function of the intensity of light received by the sensor. The rate of emission of the wireless signal may be correlated to the power available to the sensor 207. The sensor 207 can thus communicate the information about the intensity of the light at the surface 205 to the emitter 201 with changes in the rate of emission of the wireless signal. In various embodiments the wireless signal may be transmitted by turning the sensor 207 on and off. The rate emission of the wireless signal may, thus, depend on how frequently the sensor 207 is powered on. And, this may be a function of the power available to the sensor light supplied by the emitter 201.

The wireless signal may comprise a beacon that is emitted whenever enough power is available to generate the beacon. A beacon may comprise a signal that is repeated. Each repetition of the signal may comprise an emission of the beacon. The more power harvested, the more often the beacon is emitted. The less power harvested, the less often the beacon is emitted. If no power is harvested, the processing circuit 304 may not be powered and no beacon is emitted. And, a beacon emission may comprise a signal that is generated simply by turning the senor 207 on and off.

In various embodiments, the emitter 201 may respond to the wireless signal depending on the rate of the emission of the beacon from the sensor 207. As mentioned in the previous paragraph, in various embodiments, the more or less often the beacon is received, the higher or lower the intensity of the sanitizing light at the surface 205. If the beacon is emitted at a rate below a range indicative of a sanitizing intensity at the sensor 207, the emitter 201 may increase the intensity of the light emitted by the light source 203. The sensor 207 will then harvest more power from the light and emit the beacon more often If the beacon is emitted at a rate above a range indicative of a sanitizing intensity at the sensor 207, the emitter 201 may decrease the intensity of the light emitted by the light source 203. The sensor 207 may then harvest less power from the light and the rate of emission the beacon emission may be reduced. Increases and decreases in light intensity may be accomplished by varying the duty cycle of PWM signal.

In various embodiments, the processing circuit 301 may measure the light intensity at the surface 205 based on the wireless signal. In various embodiments, processing circuit 301 may determine the light intensity at the surface depending on the rate of emission detected from wireless signal broadcast by the sensor 207.

In various embodiments, the processing circuit 301 may also time the duration of periods when the beacon is emitted within a desired range. For example, the processing circuit 301 may be triggered to count clock cycles when the beacon is emitted at a rate above a lower threshold indicative of a sanitizing intensity. When enough time has passed, the processing circuit 301 may shut off the light to prevent inefficient overexposure. The processing circuit 301 may be coupled with a clock circuit. In various embodiments, the processing circuit 301 may comprise a clock circuit.

To promote accuracy of a closed-loop system 200, it may be advantageous to configure the photoelectric transducer 302 to harvest power only from a range of wavelengths of light that correspond to the wavelength of light produced by the light source 203. The photoelectric transducer 302 may thus only power the processing circuit 304 of the sensor 207 when light at the sanitizing wavelength is received. The photoelectric transducer 302 may provide a filtering operation that prevents the processing circuit 304 from being activated by environmental light that was not produced by the emitter 201, which may prevent false signals from being produced by the sensor 207 triggered by ambient light or light with a wavelength other than the desired sanitizing wavelength.

For example, a surface 205 may be located in an area with a much ambient light. Configuring a photoelectric transducer 302 to only harvest light from the desired sanitizing wavelength, may prevent the sensor 207 from being powered by the ambient light if light produced by the emitter 201 is not present. This may also prevent ambient light from interfering with operation of the sensor 207 while the emitter 201 is producing light at the desired sanitizing wavelength. For example, if light is harvested from ambient light (or light that does not have the desired sanitizing wavelength) the sensor 207 may produce false signals or the rate of production of a wireless signal produced by the sensor 207 may not correspond to the intensity of light with the desired wavelength present at the area where the sanitization operation is being performed.

Figure 4:
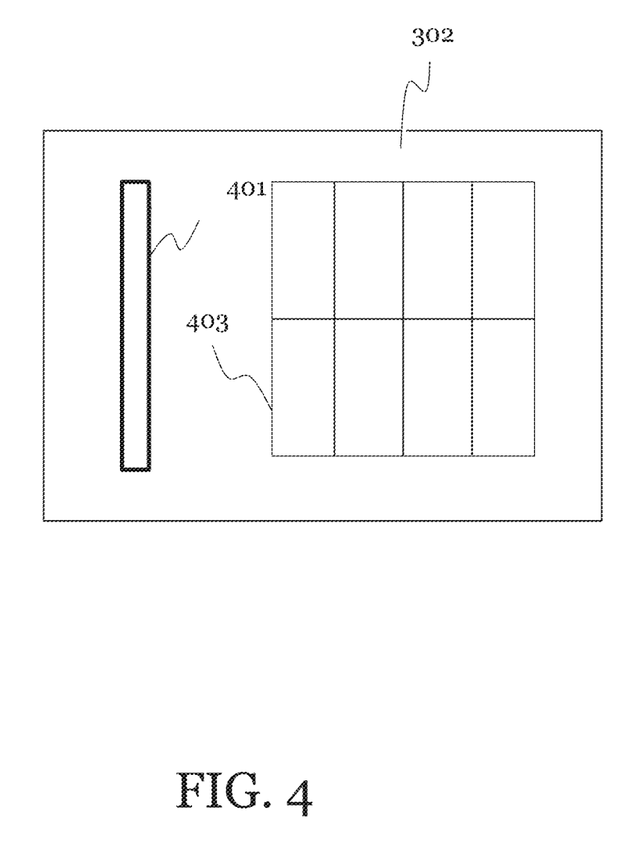
FIG. 4 depicts a photoelectric transducer consistent with an embodiment of the present invention.

FIG. 4 depicts a photoelectric transducer consistent with an embodiment of the present invention.

The photoelectric transducer 302 may comprise an optical filter 401. The optical filter 401 may comprise a passive device that may transmit light having a wavelength corresponding to the wavelength of light produced by the emitter 201. Light falling outside that wavelength may be blocked by the optical filter 401.

The photoelectric transducer 302 may also further comprise a photovoltaic cell 403. The photovoltaic cell 403 may be positioned so light passes through the optical filter 401 before reaching the photovoltaic cell 403. In various embodiments, the optical filter 401 may be affixed to the surface of the photovoltaic cell 403. The optical filter 401 may then pass light at the desired sanitizing wavelength to the photovoltaic cell 403 and block light that does not have the desires wavelength. The photovoltaic cell 403 thus may harvest power only from light with a wavelength falling in the same range as sanitizing light produced by the emitter 201. In other words, the optical filter 401 may narrow the spectrum of light received by photovoltaic cell 403. In various embodiments, the optical filter 401 may comprise a film. In various embodiments, the optical filter 401 may comprise a polymer.

Figure 5:
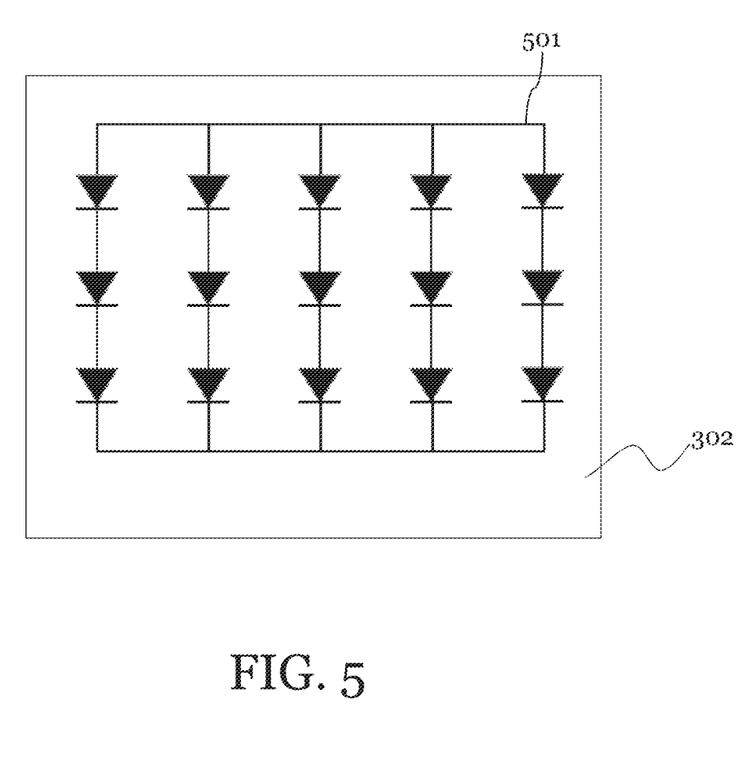
FIG. 5 depicts a photoelectric transducer consistent with an embodiment of the present invention.

FIG. 5 depicts a photoelectric transducer consistent with an embodiment of the present invention.

In various embodiments, the photoelectric transducer 302 may comprise an LED or array of LEDs 501. The LED or array of LEDs 501 may be configured to generate a current when exposed to light at a desired sanitizing wavelength. For example, the LED or array of LEDs 501 may be reverse biased. Light shining on the LED or array of LEDs 501 may produce a photocurrent.

The spectral sensitivity of the LED or array of LEDs 501 for producing the current may correspond to the wavelength of the light produced by the emitter 201. Thus, the LEDs or array of LEDs 501 will only harvest power from light at the wavelength of light produced by the emitter 201. And, the amount of power harvested may be proportional to the intensity of the light at the sanitizing wavelength at the sensor 207. The LED or array of LEDs 501 may thus comprise sensing LEDs that sense light at the sanitizing wavelength.

In various embodiments, the LED or array of LEDs 501 may be the same type of LEDs used for the light source 203 of the emitter. The spectral range of the first LED 203A or LEDs of the light source 203 may match the spectral range of the LED or array of LEDs 501 of the photoelectric transducer 302. The materials and composition of the LED or array of LEDs 501 may match the materials and composition of the LED or LEDs of the light source 203. In various embodiments, the sensor 207 may be formed in an integrated circuit. The integrated circuit may comprise the photoelectric transducer 302.

In various embodiments, where a configuration of an array of LEDs may be used for the photoelectric transducer 302, an arrangement of the LEDs may be selected according to voltage and power needs for operation of a sensor 207. For example, if a sensor 207 requires 3V to operate, three LEDs having a forward voltage of 1V each may be coupled in series. LEDs of an array of LEDs 501 may be arranged in parallel depending on power considerations for operation of the sensor 207.

Figure 6:
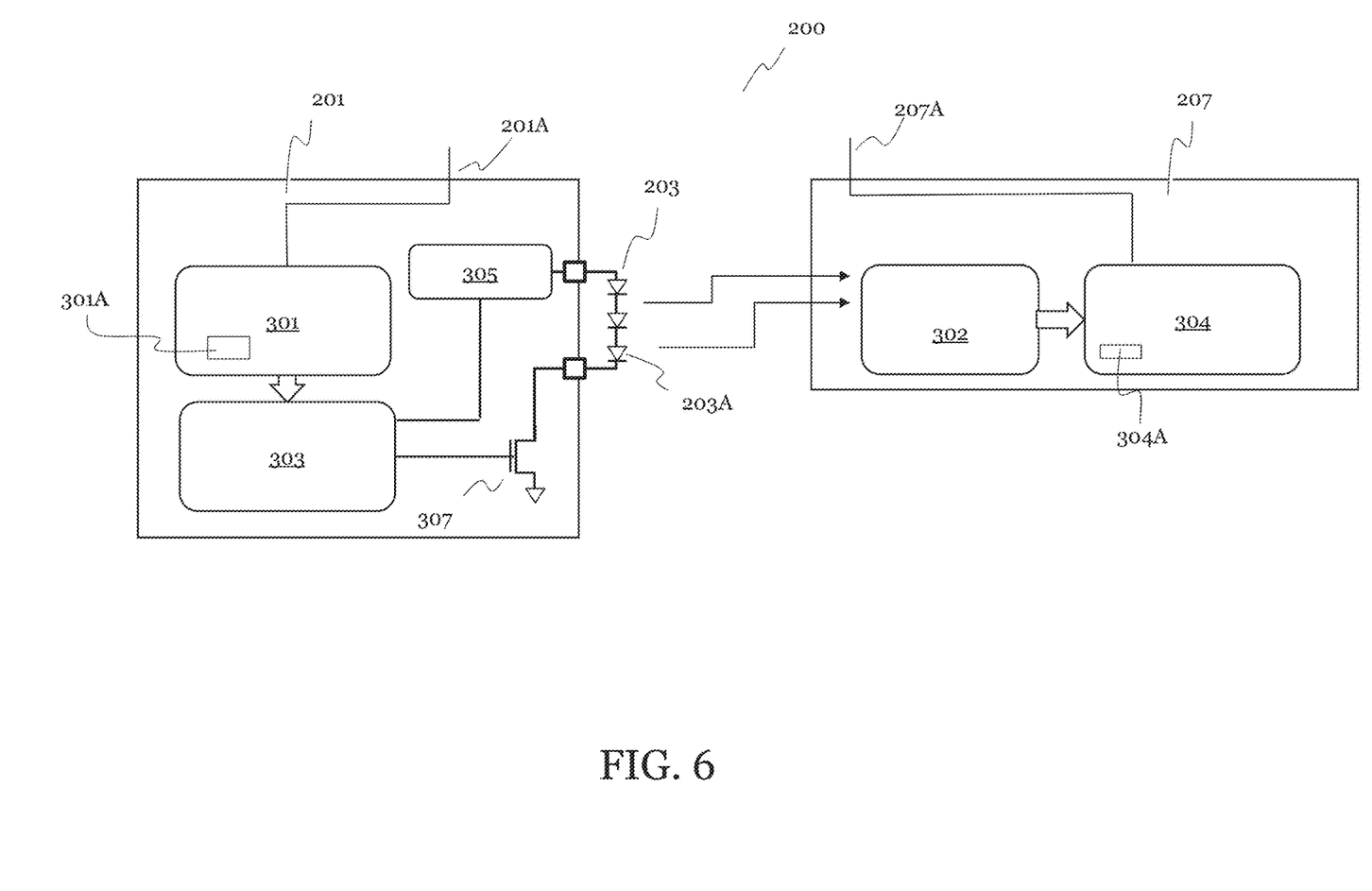
FIG. 6 depicts a closed loop system consistent with an embodiment.

FIG. 6 depicts a closed loop system consistent with an embodiment.

In various embodiments, the processing circuit 301 may comprise a memory 301A. The memory may comprise a non-transitory computer readable medium. The memory may store an instruction set that when executed causes the processing circuit 301 to increase the PWM signal when the wireless signal received by the emitter 201 from the sensor 207 is indicative of light intensity falling below a desired level. When executed, he instruction set may cause the processing circuit 301 to decrease the PWM signal when the wireless signal received by the emitter 201 from the sensor 207 is indicative of light above a desired level. When executed, he instruction set may cause the processing circuit 301 to shut off the light source 203 when the wireless signal received by the emitter 201 from the sensor 207 indicates that the light at the desired wavelength have been received by the sensor 207 for a desired duration.

In various embodiments, processing circuit 304 may comprise a memory 304A. The memory 30A may comprise a non-transitory computer readable medium. The memory 304A may store an instruction set that, when executed, causes the processing circuit 304A to control emission of a wireless signal depending on the power harvested by photoelectric transducer 302.

Figure 7:
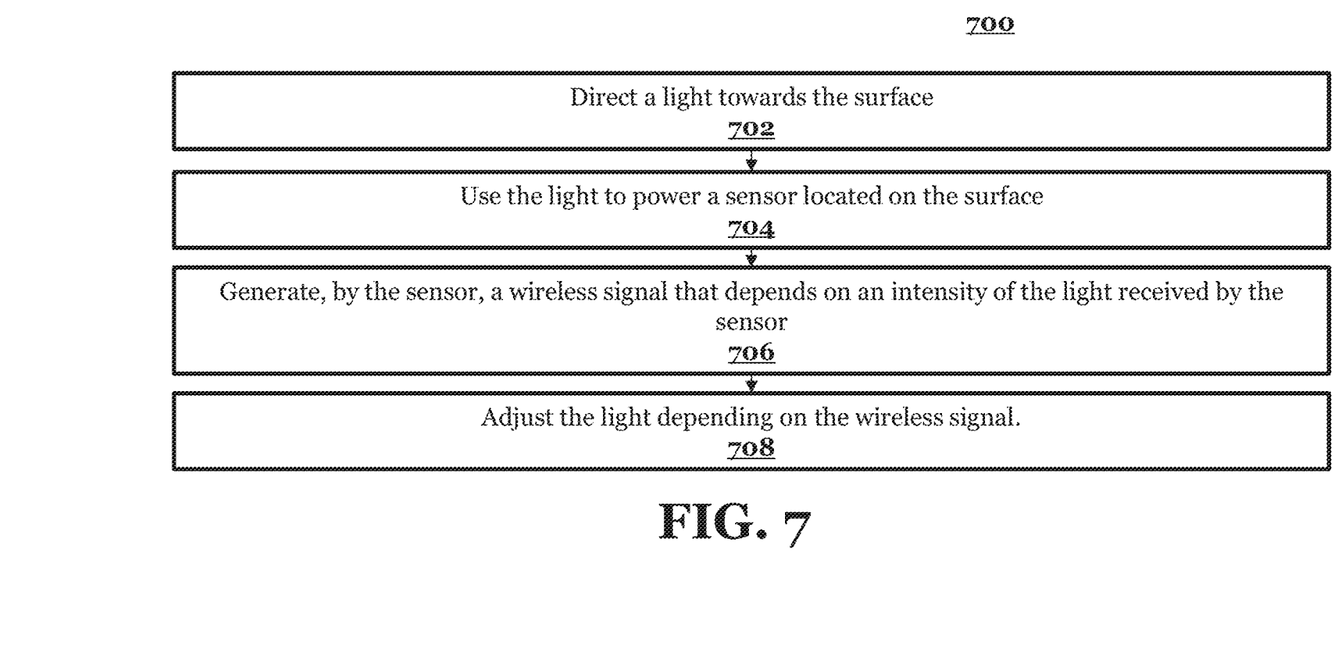
FIG. 7 depicts a method for sanitizing a surface consistent with an embodiment.

FIG. 7 depicts a method 700 for sanitizing a surface.

In various embodiments, the method 700 for sanitizing a surface comprises at a step 702 directing a light towards the surface; at a step 704 using the light to power a sensor located on the surface; at a step 706 generating, by the sensor, a wireless signal that depends on an intensity of the light received by the sensor; and at step 708 adjusting the light depending on the wireless signal.

In various embodiments, the method 700 for sanitizing a surface may further comprise determining from the wireless signal that the surface has received a desired intensity of the light for a desired duration; and shutting off the light after determining that the surface has received the desired intensity of the light for the desired duration.

In various embodiments, the method 700 for sanitizing a surface may further comprise wherein generating the wireless signal comprises emitting a beacon at an increased rate when the intensity of the light received by the sensor increases and at a decreased rate when the intensity of the light received by the sensor decreases.

In various embodiments, the method 700 for sanitizing a surface may further comprise wherein adjusting the light comprises increasing a duty cycle for a light source, decreasing the duty cycle for the light source, or both.

In various embodiments, the method 700 for sanitizing a surface may further comprise wherein the light is directed to the surface using a light emitter.

In various embodiments, the method 700 for sanitizing a surface may further comprise receiving the wireless signal by the light emitter and measuring, by the light emitter, the intensity of the light received by the sensor from the wireless signal.

In various embodiments, the method 700 for sanitizing a surface may further comprise, wherein using the light to power the sensor comprises harvesting power from the light at the surface, a magnitude of the power depending on the intensity of the received by the sensor.

In various embodiments, the method 700 for sanitizing a surface may further comprise, wherein a rate of the wireless signal depends on the magnitude of the power harvested.

Example 1. A method for sanitizing a surface, the method including: directing a light towards the surface; using the light to power a sensor located on the surface; generating, by the sensor, a wireless signal that depends on an intensity of the light received by the sensor; and adjusting the light depending on the wireless signal.

Example 2. The method of Example 1, further including determining from the wireless signal that the surface has received a desired intensity of the light for a desired duration; and shutting off the light after determining that the surface has received the desired intensity of the light for the desired duration.

Example 3. The method of Example 1 or Example 2, further including wherein generating the wireless signal comprises emitting a beacon at an increased rate when the intensity of the light received by the sensor increases and at a decreased rate when the intensity of the light received by the sensor decreases.

Example 4. The method of Example 1 to Example 3, further including wherein adjusting the light comprises varying a duty cycle for a light source.

Example 5. The method of Example 1 to Example 4, further including wherein the light is directed to the surface using a light emitter.

Example 6. The method of Example 1 to Example 5, further including receiving the wireless signal by the light emitter and measuring, by the light emitter, the intensity of the light received by the sensor from the wireless signal.

Example 7. The method of Example 1 to Example 6, further including 1, wherein using the light to power the sensor comprises harvesting power from the light at the surface, a magnitude of the power depending on the intensity of the light received by the sensor.

Example 8. The method of Example 1 to Example 7, further including, wherein a rate of the wireless signal depends on the magnitude of the power harvested.

Example 9. A system to sanitize a surface, the system including: an emitter including: a light source configured to generate light at a sanitizing wavelength; a receiver configured to receive a wireless signal; and a processing circuit for the emitter configured to turn the light source on, turn the light source off, and adjust an intensity of light generated by the light source depending on the wireless signal. The system further including a sensor including: a photoelectric transducer configured to convert light at the sanitizing wavelength to a current; and a processing circuit for the sensor powered by the current and in communication with a transmitter to transmit the wireless signal, the processing circuit for the sensor being configured to control emission of the wireless signal depending on a power level supplied by the current.

Example 10. The system of Example 9, wherein the sensor comprises an energy autonomous sensor.

Example 11. The system of Example 9 or Example 10, wherein the photoelectric transducer includes a photovoltaic cell and an optical filter configured to pass the light at the sanitizing wavelength.

Example 12. The system of Example 9 to Example 11, wherein the photoelectric transducer includes a first sensing light emitting diode.

Example 13. The system of Example 9 to Example 12, wherein the light source includes a first emitting light emitting diode.

Example 14. The system of Example 9 to Example 13, wherein the first sensing light emitting diode has a spectral sensitivity that matches a spectral range of the first emitting light emitting diode.

Example 15. The system of Example 9 to Example 14, wherein a spectral range of the first sensing light emitting diode matches a spectral range of the first emitting light emitting diode.

Example 16. The system of Example 9 to Example 15, wherein the first sensing light emitting diode is reverse biased.

Example 17. The system of Example 9 to Example 16, wherein the first sensing light emitting diode is part of an array of sensing light emitting diodes.

Example 18. The system of Example 9 to Example 17, wherein the processing circuit is configured to vary a rate of emission of the wireless signal depending on the power level.

Example 19. An energy-autonomous sensor for a closed-loop sanitization operation including: a photoelectric transducer configured to convert light at a sanitizing wavelength into a current; a transmitter to emit a wireless signal; and a processing circuit powered by the current and in communication with the transmitter, the processing circuit being configured to control emission of the wireless signal depending on a power level supplied by the current.

Example 20. The energy autonomous sensor of Example 19, wherein the processing circuit controls a rate of emission of the wireless signal depending on the power level supplied by the current.

Example 21. The energy autonomous sensor of Example 19 or Example 20, wherein the photoelectric transducer includes a photovoltaic cell and an optical filter configured to pass the light at the sanitizing wavelength.

Example 22. The energy autonomous sensor of Example 19 to Example 21, wherein the photoelectric transducer includes a first sensing light emitting diode.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method, comprising:
   directing, by a light emitter, a light towards a surface to sanitize the surface;
   using the light to power a sensor located on the surface;
   emitting, by the sensor, a wireless beacon signal based on an intensity of the light received by the sensor, wherein a frequency at which the wireless beacon signal is repeatedly emitted increases as the intensity of the light received by the sensor increases and decreases as the intensity of the light received by the sensor decreases;
   detecting, by the light emitter, the frequency at which rate of emission of the wireless beacon signal is repeatedly emitted from the sensor;
   determining, by the light emitter, whether the frequency at which the wireless beacon signal is repeatedly emitted from the sensor is below or above a threshold frequency;
   increasing, by the light emitter, the intensity of the light directed towards the surface in response to determining that the frequency at which the wireless beacon signal is repeatedly emitted from the sensor is below the threshold frequency; and
   decreasing, by the light emitter, the intensity of the light directed towards the surface in response to determining that the frequency at which the wireless beacon signal is repeatedly emitted from the sensor is above the threshold frequency.

2. The method of claim 1, further comprising:
   determining from the frequency at which the wireless beacon signal is repeatedly emitted that the surface has received a desired intensity of the light for a desired duration; and
   shutting off the light after determining that the surface has received the desired intensity of the light for the desired duration.

3. The method of claim 1, wherein emitting the wireless beacon signal comprises repeatedly emitting a same beacon signal.

4. The method of claim 1, wherein increasing or decreasing the intensity of the light comprises varying a duty cycle for a light source.

5. The method of claim 1, further comprising receiving the wireless beacon signal by the light emitter and measuring, by the light emitter, the intensity of the light received by the sensor based on the frequency at which the wireless beacon signal is repeatedly emitted.

6. The method of claim 1, wherein using the light to power the sensor comprises harvesting power from the light at the surface, a magnitude of the power depending on the intensity of the light received by the sensor.

7. The method of claim 6, wherein the frequency at which the wireless beacon signal is repeatedly emitted depends on the magnitude of the power harvested.

8. A method, comprising:
   directing, by a light emitter, a light towards a surface to sanitize the surface;
   using the light to power a sensor located on the surface;
   emitting, by the sensor, a wireless beacon signal based on an intensity of the light received by the sensor, a frequency at which the wireless beacon signal is repeatedly emitted by the sensor varying based on the intensity of the light received by the sensor; and
   adjusting, by the light emitter, the intensity of the light directed towards the surface based on the frequency at which the wireless beacon signal is repeatedly emitted from the sensor.

9. The method of claim 8, further comprising:
   determining from the frequency at which the wireless beacon signal is repeatedly emitted that the surface has received a desired intensity of the light for a desired duration; and
   shutting off the light after determining that the surface has received the desired intensity of the light for the desired duration.

10. The method of claim 8, wherein emitting the wireless beacon signal comprises repeatedly emitting a same beacon signal.

11. The method of claim 8, wherein adjusting the intensity of the light directed towards the surface comprises varying a duty cycle for a light source.

12. The method of claim 8, further comprising receiving the wireless beacon signal by the light emitter and measuring, by the light emitter, the intensity of the light received by the sensor based on the frequency at which the wireless beacon signal is repeatedly emitted.

13. The method of claim 8, wherein using the light to power the sensor comprises harvesting power from the light at the surface, a magnitude of the power depending on the intensity of the light received by the sensor.

14. The method of claim 13, wherein the frequency at which the wireless beacon signal is repeatedly emitted depends on the magnitude of the power harvested.

15. A method, comprising:
   directing, by a light emitter, a light towards a surface to sanitize the surface, the light having a sanitizing wavelength;
   using the light to power a sensor located on the surface;
   emitting, by the sensor, a wireless beacon signal when powered by the intensity of the light received by the sensor, wherein a frequency at which the wireless beacon signal is repeatedly emitted increases with higher intensities of the light received by the sensor and decreases with lower intensities of the light received by the sensor;
   monitoring, by the light emitter, changes in the frequency at which the wireless beacon signal is repeatedly emitted from the sensor; and
   dynamically adjusting, by the light emitter, an intensity of the light directed towards the surface based on the monitored changes in the frequency at which the wireless beacon signal is repeatedly emitted.

16. The method of claim 15, further comprising:
   determining from the frequency at which the wireless beacon signal is repeatedly emitted that the surface has received a desired intensity of the light for a desired duration; and
   shutting off the light after determining that the surface has received the desired intensity of the light for the desired duration.

17. The method of claim 15, wherein emitting the wireless beacon signal comprises repeatedly emitting a same beacon signal.

18. The method of claim 15, wherein dynamically adjusting the intensity of the light directed towards the surface comprises varying a duty cycle for a light source.

19. The method of claim 15, further comprising receiving the wireless beacon signal by the light emitter and measuring, by the light emitter, the intensity of the light received by the sensor based on the frequency at which the wireless beacon signal is repeatedly emitted.

20. The method of claim 15, wherein using the light to power the sensor comprises harvesting power from the light at the surface, a magnitude of the power depending on the intensity of the light received by the sensor.

* * * * *

UNITED STATES PATENT AND TRADEMARK OFFICE
CERTIFICATE OF CORRECTION

PATENT NO. : 12,285,534 B2  
APPLICATION NO. : 17/328435  
DATED : April 29, 2025  
INVENTOR(S) : La Rosa et al.

Page 1 of 1

It is certified that error appears in the above-identified patent and that said Letters Patent is hereby corrected as shown below:

In the Claims

In Column 12, Line 44, Claim 15:
Change "powered by the intensity of the light received by" to --powered by the light received by--

Signed and Sealed this
Tenth Day of June, 2025

Coke Morgan Stewart
*Acting Director of the United States Patent and Trademark Office*